(12) United States Patent
Horng et al.

(10) Patent No.: US 8,698,636 B2
(45) Date of Patent: Apr. 15, 2014

(54) WIRELESS DETECTION APPARATUS AND METHOD

(75) Inventors: Tzyy-Sheng Horng, Kaohsiung (TW);
Fu-Kang Wang, Kaohsiung (TW);
Chieh-Hsun Hsiao, Kaohsiung (TW);
Je-Kuan Jau, Tainan (TW)

(73) Assignees: Industrial Technology Research Institute, Hsinchu (TW); National Sun Yat-sen University, Kaohsiung (TW)

( * ) Notice: Subject to any disclaimer, the term of this patent is extended or adjusted under 35 U.S.C. 154(b) by 373 days.

(21) Appl. No.: 12/886,522

(22) Filed: Sep. 20, 2010

(65) Prior Publication Data

US 2011/0279275 A1 Nov. 17, 2011

(30) Foreign Application Priority Data

May 17, 2010 (TW) .............................. 99115691 A

(51) Int. Cl.
*G08B 23/00* (2006.01)
(52) U.S. Cl.
USPC ................... 340/573.1; 340/555; 340/815.45
(58) Field of Classification Search
USPC ...................... 340/573.1, 942, 956, 468, 555, 340/310.12–310.13, 332, 815.45, 815.53, 340/815.66, 815.76
See application file for complete search history.

(56) References Cited

U.S. PATENT DOCUMENTS

| | | | |
|---|---|---|---|
| 3,793,626 A * | 2/1974 | Zambuto | 340/870.09 |
| 4,261,370 A * | 4/1981 | von Nettelhorst | 600/515 |
| 4,517,982 A | 5/1985 | Shiga et al. | |
| 4,958,638 A | 9/1990 | Sharpe et al. | |
| 4,991,585 A | 2/1991 | Mawhinney | |
| 5,774,795 A * | 6/1998 | Ando | 455/106 |
| 6,133,802 A * | 10/2000 | Ma | 331/172 |
| 7,740,588 B1 * | 6/2010 | Sciarra | 600/484 |
| 2005/0073424 A1 * | 4/2005 | Ruoss et al. | 340/686.6 |
| 2007/0047970 A1 * | 3/2007 | Tsuji | 398/198 |
| 2008/0146944 A1 | 6/2008 | Tao et al. | |
| 2009/0278728 A1 * | 11/2009 | Morgan et al. | 342/115 |
| 2009/0290066 A1 * | 11/2009 | Lin | 348/572 |
| 2011/0148884 A1 * | 6/2011 | Zeleny | 345/441 |

FOREIGN PATENT DOCUMENTS

| | | |
|---|---|---|
| CN | 101489478 | 7/2009 |
| WO | 2006115704 | 11/2006 |
| WO | 2009124297 | 10/2009 |

OTHER PUBLICATIONS

"First Office Action of China counterpart application" issued on Jul. 3, 2012, p. 1-p. 6.

* cited by examiner

*Primary Examiner* — Daniel Previl
(74) *Attorney, Agent, or Firm* — Jianq Chyun IP Office

(57) ABSTRACT

A wireless detection apparatus includes an antenna, a voltage control oscillator, and a processing unit. The antenna receives a first wireless signal and generates an electrical signal according to the first wireless signal. The first wireless signal is generated by reflecting a second wireless signal from an object under test. The voltage control oscillator is coupled to the antenna to generate an oscillating signal under an interference of the electrical signal. The oscillating signal varies with variation of the electrical signal. The processing unit is coupled to the voltage control oscillator to evaluate a parameter of the object under test according to the variation of the oscillating signal.

21 Claims, 4 Drawing Sheets

WIRELESS DETECTION APPARATUS AND METHOD

CROSS-REFERENCE TO RELATED APPLICATION

This application claims the priority benefit of Taiwan application serial no. 99115691, filed on May 17, 2010. The entirety of the above-mentioned patent application is hereby incorporated by reference herein and made a part of this specification.

BACKGROUND

1. Technical Field

The disclosure relates to a wireless detection apparatus and a wireless detection method.

2. Description of Related Art

In recent years, with the improvement of people's life, people have started paying attention to their health problems. Since the majority of people ignore alerting signals sent by their bodies, they often didn't realize their health problems before their health conditions or living environments become worse. Accordingly, in order to allow ordinary people to observe their physiological conditions on their own, various measurement instruments have been introduced. As such, ordinary people can use various measurement instruments to monitor physiological changes in their bodies, such that they can timely perceive their health problems and therefore have proper rest according to their physical fitness.

There are generally two types of designs of the conventional physiological signal detection circuit. One is the contact type physiological signal detector, and the other is the non-contact type physiological signal detector. Contact type physiological signal detectors generally perform the measurement by contacting human bodies. The contact type physiological signal detectors have simple circuit architecture. However, because of the necessity of contacting the human body, the detection circuit may make the user feel uncomfortable if the detector is used for a long time.

On the other hand, non-contact type physiological signal detectors are generally constructed on the basis of Doppler radar. In a conventional Doppler radar construction, a sinusoidal signal is generated and transmitted through a power splitter. One way of outputs of the power splitter is connected to an antenna so as to radiate the sinusoidal signal to the human thorax. The sinusoidal signal experiences a Doppler effect due to the up and down movement of the thoracic wall. After the reflected signal and the signal from another output of the power splitter are mixed through a mixer and undergo subsequent processing, physiological information for observation can be obtained. However, in this physiological signal detector, the phase difference between the reflected wave and the wave from the another output of the power splitter may cause a destructive interference and therefore lead to a detection zero-point at some particular positions where detection is made impossible, which limits the use of this non-contact type detector. In addition, this type of detector has complex circuit architecture, high power consumption and high cost. Furthermore, the detecting results may be inconsistent due to variation of the detecting distance.

SUMMARY

In one exemplary embodiment, a wireless detection apparatus is introduced herein, which includes a first antenna, a voltage control oscillator, and a processing unit. The first antenna is adapted to receive a first wireless signal and generate an electrical signal according to the first wireless signal. The first wireless signal is generated by reflecting a second wireless signal from an object under test. The voltage control oscillator is coupled to the first antenna and adapted to generate an oscillating signal under an interference of the electrical signal. The oscillating signal varies with variation of the electrical signal. The processing unit is coupled to the voltage control oscillator and adapted to evaluate a parameter of the object under test according to the variation of the oscillating signal.

In another exemplary embodiment, a wireless detection apparatus is introduced herein, which includes a photoelectric converter, a voltage control oscillator, and a processing unit. The photoelectric converter is adapted to receive a first light signal and generate an electrical signal according to the first light signal. The first light signal is generated by an object under test by reflecting a second light signal. The voltage control oscillator is coupled to the photoelectric converter and adapted to generate an oscillating signal under an interference of the electrical signal. The oscillating signal varies with variation of the electrical signal. The processing unit is coupled to the voltage control oscillator and adapted to evaluate a movement parameter of the object under test according to the variation of the oscillating signal.

In another exemplary embodiment, a wireless detection apparatus is introduced herein, which includes an antenna and a voltage control oscillator. The antenna is adapted to receive a first wireless signal and generate an electrical signal according to the first wireless signal, wherein the first wireless signal is generated by reflecting a second wireless signal from an object under test. The voltage control oscillator is coupled to the antenna and adapted to generate an oscillating signal under an interference of the electrical signal. The oscillating signal varies with variation of the electrical signal. The oscillating signal is used to evaluate a parameter of the object under test.

In another exemplary embodiment, a wireless detection apparatus is introduced herein, which includes a photoelectric converter and a voltage control oscillator. The photoelectric converter is adapted to receive a first light signal and generate an electrical signal according to the first light signal. The first light signal is generated by an object under test by reflecting a second light signal. The voltage control oscillator is coupled to the photoelectric converter and adapted to generate an oscillating signal under an interference of the electrical signal. The oscillating signal varies with variation of the electrical signal. The oscillating signal is used to evaluate a movement parameter of the object under test.

In another exemplary embodiment, a wireless detection method is introduced herein. In this wireless detection method, a first wireless signal is received and an electrical signal is generated according to the first wireless signal using an antenna. The first wireless signal is generated by reflecting a second wireless signal from an object under test. An oscillating signal is generates a voltage control oscillator under an interference of the electrical signal. The oscillating signal varies with variation of the electrical signal. The oscillating signal is used to evaluate a parameter of the object under test.

In still another exemplary embodiment, a wireless detection method is introduced herein. In this wireless detection method, a received first light signal is converted into an electrical signal using a photoelectric converter. The first light signal is generated by reflecting a second light signal from an object under test. An oscillating signal is generated by a voltage control oscillator under an interference of the electrical signal. The oscillating signal varies with variation of the electrical signal. The oscillating signal is used to evaluate a movement parameter of the object under test.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF THE EMBODIMENTS

An injection-locking technique is used to receive and amplify the phase modulation caused by the up and down movement of the thoracic wall due to Doppler effect. Assume that an injection signal is applied to an oscillator; injection locking holds under the condition that the spontaneous frequency separation between the inherent oscillation and injection frequencies is smaller than the oscillator's locking range. And the output frequency is pulled from inherent oscillation frequency to said injection signal's frequency. Since the locking range is proportional to spontaneous frequency separation and magnitude ratio from injection signal to inherent oscillation signal, an oscillator can synchronize with a low-level injection power level for vital sign sensing.

Figure 1:
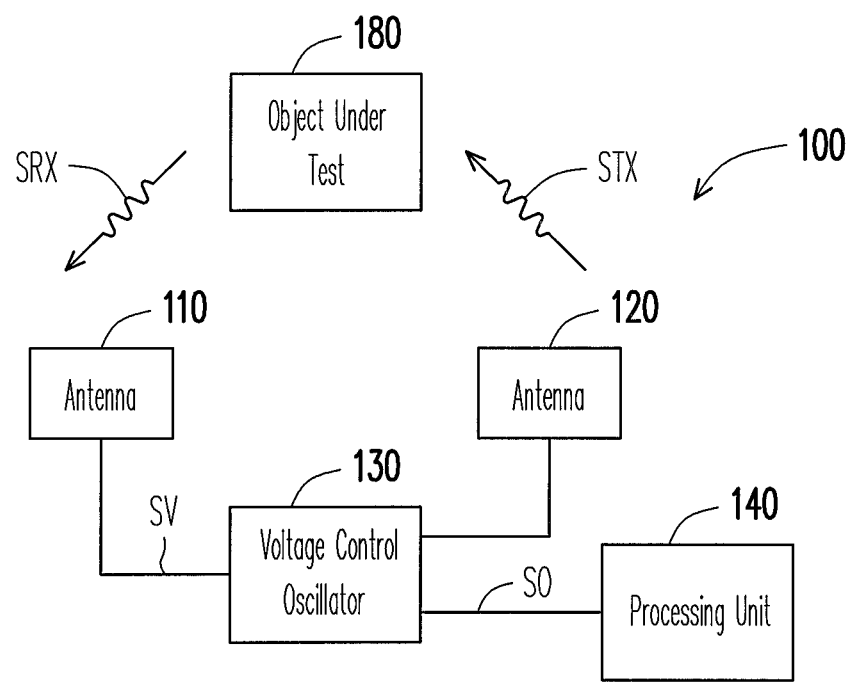
FIG. 1 is a block diagram showing a wireless detection apparatus according to one exemplary embodiment.

FIG. 1 is a block diagram of a wireless detection apparatus according to one exemplary embodiment. Referring to FIG. 1, the wireless detection apparatus 100 includes antennas 110, 120, a voltage control oscillator 130, and a processing unit 140. The antenna 110 (e.g. a receiving antenna) receives a first wireless signal (e.g. an RF-modulated signal) SRX and generates an electrical signal SV according to the first wireless signal SRX. The voltage control oscillator 130 is coupled to the antenna 110 and generates an oscillating signal SO under an interference of the electrical signal SV. The oscillating signal SO varies with variation of the electrical signal SV. In the present embodiment, under an interference of the electrical signal SV, the voltage control oscillator 130 generates the oscillating signal SO by enabling a self injection lock function.

The processing unit 140 is coupled to the voltage control oscillator 130 and evaluates a parameter of an object under test 180 according to the variation of the oscillating signal SO. The antenna 120 (e.g. a transmitting antenna) is coupled to the voltage control oscillator 130 to receive the oscillating signal SO and generates a second wireless signal STX to the object under test 180 according to the oscillating signal SO, such that the object under test 180 reflects the second wireless signal STX to generate the first wireless signal SRX. In the present embodiment, the object under test 180 is, for example, a human body and the parameter of the object under test 180 is, for example, a parameter is heartbeat, pulse, breath, movements (e.g. body movements), or any combination thereof. In addition, the frequency of the first wireless signal SRX is different from the frequency of the second wireless signal STX.

Operation of the wireless detection apparatus 100 is explained below. Firstly, the antenna 120 emits the second wireless signal STX to the object under test (human body) 180, and the object under test 180 reflects the second wireless signal STX to generate the first wireless signal SRX to the antenna 110. In the present embodiment, due to the breath, up and down movements of heartbeat, pulse, or body movements, the second wireless signal STX experiences a Doppler effect. Therefore, the first wireless signal SRX generated by reflecting the second wireless signal STX has different frequencies and the frequency of the first wireless signal SRX is also different from the frequency of the second wireless signal STX. Then, the antenna 110 receives the first wireless signal SRX and generates the electrical signal SV to the voltage control oscillator 130 according to the first wireless signal SRX, and the voltage control oscillator 130 generates the oscillating signal SO to the processing unit 140 according to the electrical signal SV. The oscillating signal SO carries information relating to the heartbeat, breath, pulse or movements of a human body (i.e. parameter of the object under test 180). Afterwards, the processing unit 140 processes the oscillating signal SO to obtain the information relating to the heartbeat, breath, pulse or movements, allowing the user to evaluate his or her current health condition according to the obtained information.

Figure 2:
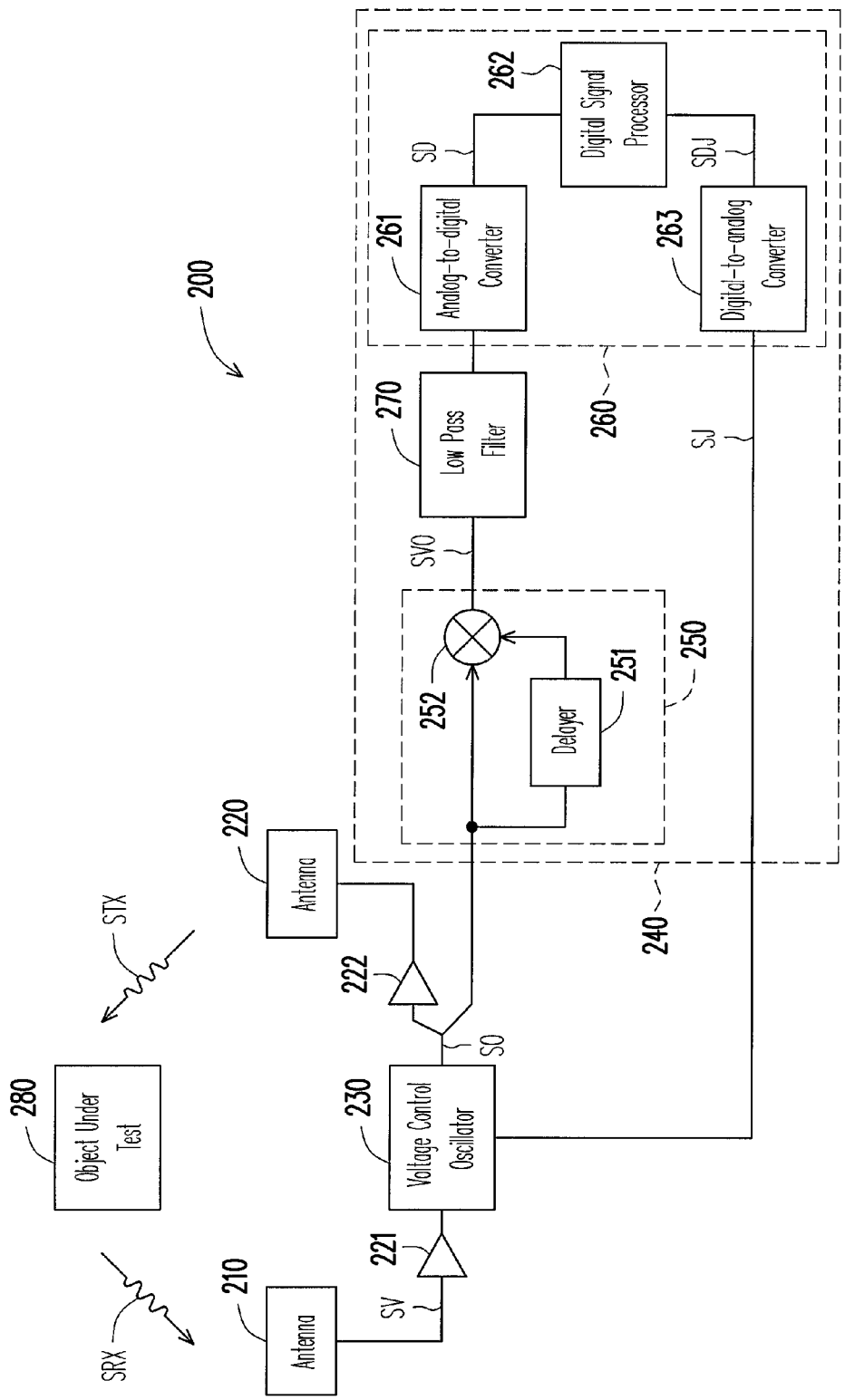
FIG. 2 is a block diagram showing a detailed circuit of the wireless detection apparatus of FIG. 1.

FIG. 2 is a detailed circuit block diagram of the wireless detection apparatus 100 of FIG. 1. Referring to FIG. 2, the wireless detection apparatus 200 includes antennas 210, 220, amplifiers 221, 222, a voltage control oscillator 230, and a processing unit 240. In the present embodiment, the implementation of the antenna 210 (e.g. receiving antenna), antenna 220 (e.g. transmitting antenna), and voltage control oscillator 230 can be the same as that of the antennas 110, 120 and voltage control oscillator 130 of FIG. 1 and therefore explanation thereof is not repeated herein.

The amplifier (e.g. a low noise amplifier) 221 is coupled between the antenna 210 and the voltage control oscillator 230, for amplifying the electrical signal SV generated by the antenna 210. The amplifier (e.g. a power amplifier) 222 is coupled between the voltage control oscillator 230 and the antenna 220, for amplifying the oscillating signal SO generated by the voltage control oscillator 230.

The processing unit 240 includes a demodulation unit 250 and a signal processing unit 260. The demodulation unit 250 is coupled to the voltage control oscillator 230 to receive the oscillating signal SO and demodulate the oscillating signal SO into a voltage signal SVO. The signal processing unit 260 is coupled to the demodulation unit 250 and processes the voltage signal SVO to obtain a processing result and an adjustment signal SJ. The signal processing unit 260 also transmits the adjustment signal SJ to the voltage control oscillator 230 to adjust the oscillating frequency of the oscillating signal SO generated by the voltage control oscillator 230. The processing result is the parameter of the object under test 280 (i.e. information relating to the heartbeat, breath or pulse of a human body), such that the user can become aware of his or her heath condition according to the processing result.

In addition, the processing unit 240 may further include a low pass filter 270. The low pass filter 270 may be coupled to the demodulation unit 250 and the signal processing unit 260 to perform low pass filtering on the voltage signal SVO to filter out high-frequency noises from the voltage signal SVO.

In addition, in the present embodiment, the demodulation unit 250 includes a delayer 251 and a mixer 252. The delayer 251 is coupled to the voltage control oscillator 230 for delaying the oscillating signal SO. The mixer 252 is coupled to the voltage control oscillator 230 and the delayer 251 for mixing the oscillating signal SO and the delayed oscillating signal SO to perform a frequency demodulation to thereby generate the voltage signal SVO.

The signal processing unit 260 includes an analog-to-digital converter 261, a digital signal processor 262, and a digital-to-analog converter 263. The analog-to-digital converter 261 is coupled to the demodulation unit 250 to perform an analog-to-digital conversion on the voltage signal SVO to generate a digital signal SD. The digital signal processor 262 is coupled to the analog-to-digital convertor 261 to process the digital signal SD to generate the processing result (i.e. obtain the parameter of the object under test 280). In addition, the digital signal processor 262 controls the digital adjustment signal SDJ to determine the output frequency of the voltage control oscillator 230. The digital-to-analog converter 263 is coupled to the digital signal processor 262 to perform a digital-to-analog conversion on the digital adjustment signal SDJ to generate the adjustment signal SJ. The adjustment signal SJ is then transmitted to the voltage control oscillator 230 to adjust the oscillating frequency of the oscillating signal SO generated by the voltage control oscillator 230.

In the wireless detection apparatus 100 as described above, the antenna (transmitting antenna) 120 is coupled to the voltage control oscillator 130, and the voltage control oscillator 130 is coupled to the antenna (receiving antenna) 110. Therefore, the frequency of the second wireless signal STX generated by the antenna 120 varies with the variation of the first wireless signal SRX. That is, the frequency of the second wireless signal STX keeps changing. However, this should not be regarded as limiting. In another example described below, the frequency of the second wireless signal STX maintains constant.

Figure 3:
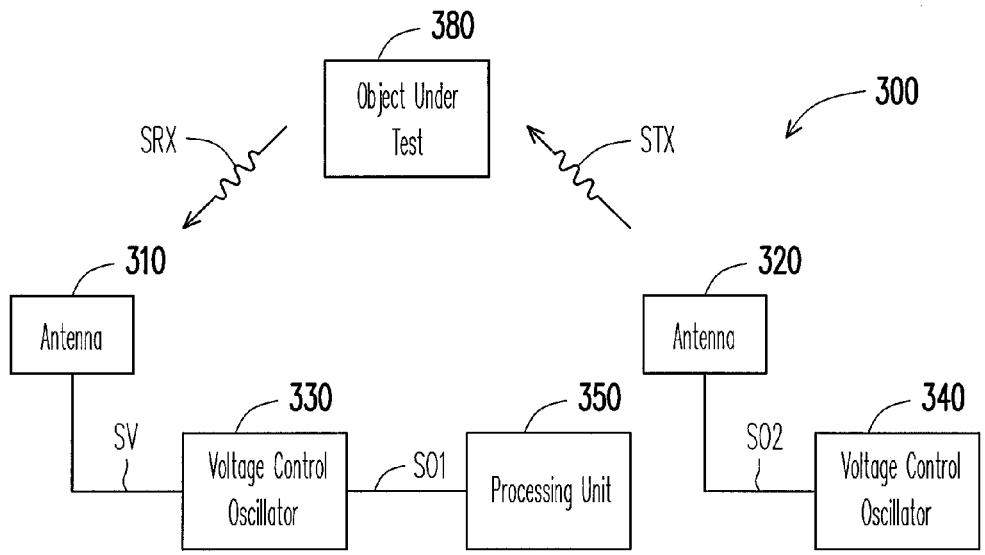
FIG. 3 is a block diagram showing a wireless detection apparatus according to another exemplary embodiment.

FIG. 3 is a block diagram of a wireless detection apparatus according to another exemplary embodiment. Referring to FIG. 3, the wireless signal detection apparatus 300 includes an antenna 310 (e.g. a receiving antenna), an antenna 320 (e.g. a transmitting antenna), voltage control oscillators 330, 340, and a processing unit 350. The implementation of the antenna 310, the voltage control oscillator 330 and the processing unit 350 may be the same as that of the antenna 110, the voltage control oscillator 130 and the processing unit 140 of FIG. 1 and therefore explanation thereof is not repeated.

In the present embodiment, the voltage control oscillator 340 can generate a second voltage control signal SO2. The antenna 320 is coupled to the voltage control oscillator 340 to receive the second voltage control signal SO2 and generate a second wireless signal STX to the object under test 380 according to the second voltage control signal SO2, such that the object under test 380 reflects the second wireless signal STX to generate a first wireless signal SRX. The antenna (transmitting antenna) 320 generates the second wireless signal STX according to the second oscillating signal SO2 outputted by the voltage control oscillator 340 rather than according to the first oscillating signal SO1 outputted by the voltage control oscillator 330. Therefore, the difference between the wireless detection apparatus 300 of FIG. 3 and the wireless detection apparatus 100 of FIG. 1 lies in that the frequency of the second wireless signal STX of FIG. 3 can maintain constant while the second wireless signal STX of FIG. 1 is variable. It is noted, however, that they are different only in the second wireless signals STX. The wireless detection apparatus 300 of FIG. 3 can be implemented in a similar manner and achieve the similar result as in the wireless detection apparatus 100 of FIG. 1 and therefore explanation thereof is not repeated herein.

In the embodiments of FIG. 1, FIG. 2 and FIG. 3 as described above, the parameter of the object under test is detected and evaluated by transmitting the wireless signal to the object under test and receiving the wireless signal reflected from the object under test. However, this should not be regarded as limiting. The principle of the present disclosure is further explained by way of another exemplary embodiment below.

Figure 4:
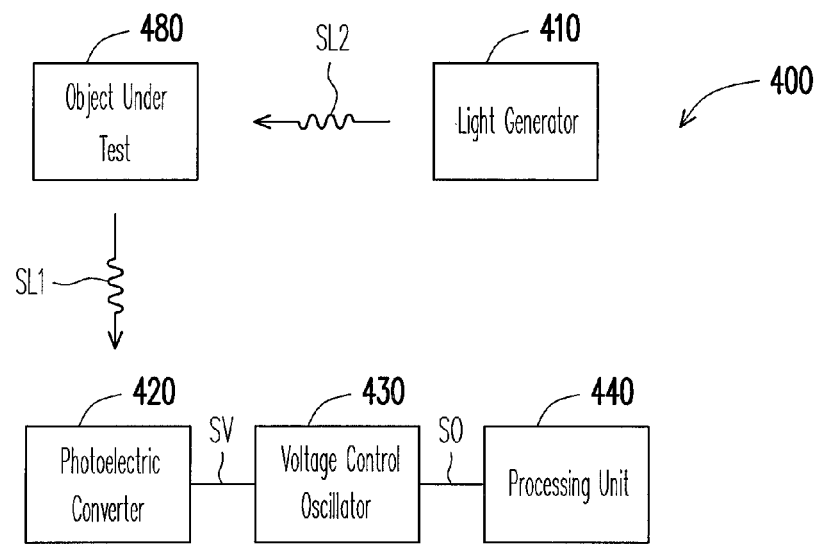
FIG. 4 is a block diagram showing a wireless detection apparatus according to still another exemplary embodiment.

FIG. 4 illustrates a block diagram of a wireless detection apparatus according to still another exemplary embodiment. Referring to FIG. 4, the wireless detection apparatus 400 includes a light generator or light source 410, a photoelectric converter 420, a voltage control oscillator 430, and a processing unit 440.

The light source 410 generates a second light signal SL2 to an object under test 480 and the object under test 480 reflects the second light signal SL2 to generate a first light signal SL1. The photoelectric converter 420 receives the first light signal SL1 and generates an electrical signal SV according to the first light signal SL1. In another embodiment, the light source 410 and the photoelectric converter 420 may be integrated into a module thus reducing the number of circuit components.

The voltage control oscillator 430 is coupled to the photoelectric converter 420 to generate an oscillating signal SO under the interference of the electrical signal SV. The oscillating signal SO varies with variation of the electrical signal SV. The processing unit 440 is coupled to the voltage control oscillator 430 to evaluate movement parameters (e.g. speed, displacement and movement frequency) of the object under test 480 according to the variation of the oscillating signal SO. The implementation of the voltage control oscillator 430 and the processing unit 440 may be the same as that of the voltage control oscillator 230 and the processing unit 240 of FIG. 2 and therefore explanation thereof is not repeated.

In the present embodiment, the second light signal SL2 also experiences a Doppler effect due to the relative movement of the object under test 480. Therefore, the first light signal SL1 generated by the object under test 480 by reflecting the second light signal SL2 have different wavelengths, and the wavelength of the first light signal SL1 is also different from the wavelength of the second light signal SL2. The photoelectric converter 420 then converts the received first light signal SL1 into the electrical signal SV and transmits the electrical signal SV to the voltage control oscillator 430. Afterwards, the voltage control oscillator 430 generates an oscillating signal SO to the processing signal 440 according to the electrical signal SV, and this oscillating signal SO carries information relating to movement of the object under test 480. The processing unit 440 then processes the oscillating signal SO to obtain the information relating to the movement of the object under test 480.

Figure 5:
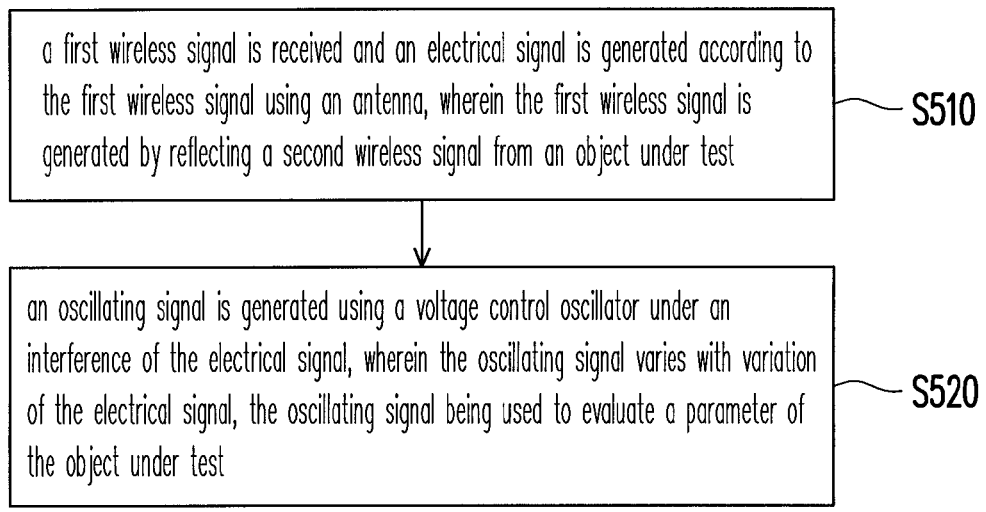
FIG. 5 is a flow diagram showing a wireless detection method according to one exemplary embodiment.

According to the embodiment of FIG. 1, a wireless detection method can be summarized and described as follows. FIG. 5 is a flow diagram showing a wireless detection method according to one exemplary embodiment. Referring to FIG. 5, in step S510, a first wireless signal is received and an electrical signal is generated according to the first wireless signal using an antenna, wherein the first wireless signal is generated by reflecting a second wireless signal from an object under test. In step S520, an oscillating signal is generated using a voltage control oscillator under an interference of the electrical signal, wherein the oscillating signal varies with variation of the electrical signal, the oscillating signal being used to evaluate a parameter of the object under test.

Figure 6:
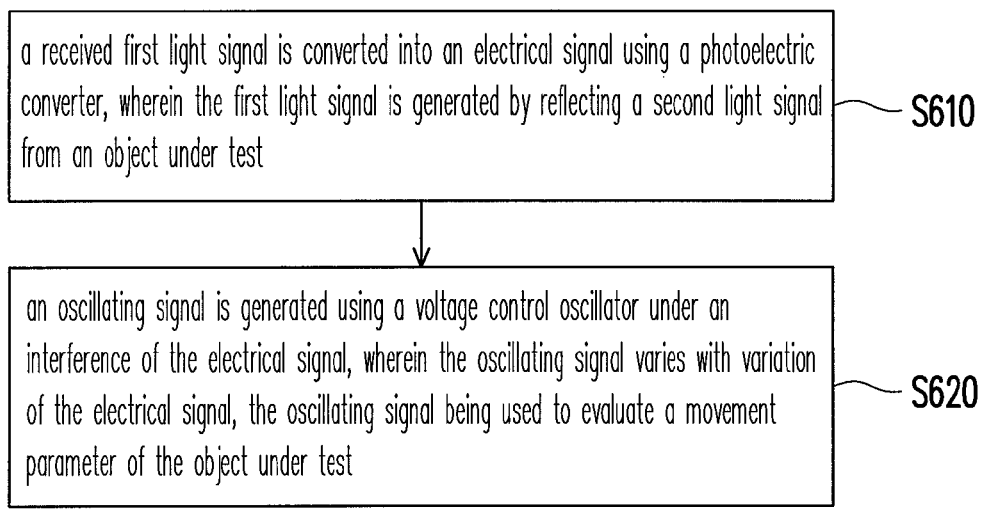
FIG. 6 is a flow diagram showing a wireless detection method according to another exemplary embodiment.

According to the embodiment of FIG. 4, a wireless detection method can be summarized and described as follows. FIG. 6 is a flow diagram showing a wireless detection method according to another exemplary embodiment. Referring to FIG. 6, in step S610, a received first light signal is converted into an electrical signal using a photoelectric converter, wherein the first light signal is generated by reflecting a second light signal from an object under test. In step S620, an oscillating signal is generated using a voltage control oscillator under an interference of the electrical signal, wherein the oscillating signal varies with variation of the electrical signal, the oscillating signal being used to evaluate a movement parameter of the object under test.

In summary, the present wireless detection apparatus is a non-contact detection apparatus in which the second wireless signal (or second light signal) transmitted to the object under test is affected by breath, heartbeat, pulse or movements (e.g. body movements) to produce the Doppler effect such that the first wireless signal (or first light signal) generated by the object under test by reflecting the second wireless signal (or second light signal) has a frequency variation corresponding to the breath, heartbeat, pulse or movements, and the voltage control oscillator generates the oscillating signal influenced by the Doppler effect by means of the self injection lock function of the voltage control oscillator. The oscillating signal is then processed by the processing unit to obtain the parameter of the object under test (e.g. information relating to the breath, heartbeat, pulse or movements) for further evaluation.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A wireless detection apparatus comprising:
   a first antenna adapted to receive a first wireless signal and generate an electrical signal according to the first wireless signal, wherein the first wireless signal is generated by reflecting a second wireless signal from an object under test;
   a voltage control oscillator coupled to the first antenna and adapted to generate an oscillating signal under an injection of the electrical signal, wherein a feedback injection locking function is employed by the voltage control oscillator, a frequency of the oscillating signal is varied and pulled by a variation of the frequency of the electrical signal; and
   a processing unit coupled to the voltage control oscillator and adapted to evaluate movement parameters of the object under test according to a variation of the frequency of the oscillating signal, wherein the oscillating signal is transmitted to the processing unit and processed by the processing unit to obtain the movement parameters of the object under test.

2. The wireless detection apparatus according to claim 1, wherein the frequency of the first wireless signal is different from the frequency of the second wireless signal due to Doppler Effects caused by the movement of the object under test.

3. The wireless detection apparatus according to claim 1, further comprising a second antenna coupled to the voltage control oscillator and adapted to receive the oscillating signal and generate the second wireless signal to the object under test according to the oscillating signal.

4. The wireless detection apparatus according to claim 3, further comprising an amplifier coupled between the voltage control oscillator and the second antenna and adapted to amplify the oscillating signal.

5. The wireless detection apparatus according to claim 1, further comprising:
   a second voltage control oscillator adapted to generate a second oscillating signal; and
   a second antenna coupled to the second voltage control oscillator and adapted to receive the second oscillating signal and generate the second wireless signal to the object under test according to the second oscillating signal.

6. The wireless detection apparatus according to claim 1, wherein the parameter of the object under test is heartbeat, pulse, breath and movements, or any combination thereof.

7. The wireless detection apparatus according to claim 1, wherein the processing unit comprises:
   a demodulation unit coupled to the voltage control oscillator and adapted to receive the oscillating signal and demodulate the oscillating signal into a voltage signal; and
   a signal processing unit coupled to the demodulation unit and adapted to process the voltage signal to obtain a processing result and an adjustment signal and transmit the adjustment signal to the voltage control oscillator.

8. The wireless detection apparatus according to claim 7, wherein the demodulation unit comprises:
   a delayer coupled to the voltage control oscillator and adapted to delay the oscillating signal; and
   a mixer coupled to the voltage control oscillator and the delayer and adapted to mix the oscillating signal and the delayed oscillating signal to generate the voltage signal.

9. The wireless detection apparatus according to claim 7, wherein the signal processing unit comprises:
   an analog-to-digital converter coupled to the demodulation unit and adapted to perform an analog-to-digital conversion on the voltage signal to generate a digital signal;
   a digital signal processor coupled to the analog-to-digital converter and adapted to process the digital signal to generate the processing result and a digital adjustment signal; and
   a digital-to-analog converter coupled to the digital signal processor and adapted to perform a digital-to-analog conversion on the digital adjustment signal to generate the adjustment signal.

10. The wireless detection apparatus according to claim 7, further comprising a low pass filter coupled between the demodulation unit and the signal processing unit to perform filtering on the voltage signal.

11. The wireless detection apparatus according to claim 1, further comprising an amplifier coupled between the first antenna and the voltage control oscillator to amplify the electrical signal.

12. A wireless detection apparatus comprising:
   a photoelectric converter adapted to receive a first light signal and generate an electrical signal according to the first light signal, wherein the first light signal is generated reflecting a second light signal from an object under test;
   a voltage control oscillator coupled to the photoelectric converter and adapted to generate an oscillating signal under an injection of the electrical signal, wherein a feedback injection locking function is employed by the voltage control oscillator, a frequency of the oscillating signal is varied and pulled by a variation of the frequency of the electrical signal; and a processing unit coupled to the voltage control oscillator and adapted to evaluate a movement parameter of the object under test according to a variation of the frequency of the oscillating signal, wherein the oscillating signal is transmitted to the processing unit and processed by the processing unit to obtain the movement parameters of the object under test.

13. The wireless detection apparatus according to claim 12, further comprising a light generator adapted to generate the second light signal to the object under test.

14. The wireless detection apparatus according to claim 12, wherein the processing unit comprises:
   a demodulation unit coupled to the voltage control oscillator and adapted to receive the oscillating signal and demodulate the oscillating signal into a voltage signal; and
   a signal processing unit coupled to the demodulation unit and adapted to process the voltage signal to obtain a processing result and an adjustment signal and transmit the adjustment signal to the voltage control oscillator.

15. The wireless detection apparatus according to claim 14, wherein the demodulation unit comprises:
   a delayer coupled to the voltage control oscillator and adapted to delay the oscillating signal; and
   a mixer coupled to the voltage control oscillator and the delayer and adapted to mix the oscillating signal and the delayed oscillating signal to generate the voltage signal.

16. The wireless detection apparatus according to claim 14, wherein the signal processing unit comprises:
   an analog-to-digital converter coupled to the demodulation unit and adapted to perform an analog-to-digital conversion on the voltage signal to generate a digital signal;
   a digital signal processor coupled to the analog-to-digital converter and adapted to process the digital signal to generate the processing result and a digital adjustment signal; and
   a digital-to-analog converter coupled to the digital signal processor and adapted to perform a digital-to-analog conversion on the digital adjustment signal to generate the adjustment signal.

17. The wireless detection apparatus according to claim 14, further comprising a low pass filter coupled between the demodulation unit and the signal processing unit to perform filtering on the voltage signal.

18. A wireless detection apparatus comprising:
   an antenna adapted to receive a first wireless signal and generate an electrical signal according to the first wireless signal, wherein the first wireless signal is generated by reflecting a second wireless signal from an object under test; and
   a voltage control oscillator coupled to the antenna and adapted to generate an oscillating signal under an injection of the electrical signal, wherein a feedback injection locking function is employed by the voltage control oscillator, a frequency of the oscillating signal is varied and pulled by a variation of the frequency of the electrical signal, the oscillating signal is processed for obtaining movement parameters of the object under test.

19. A wireless detection apparatus comprising:
   a photoelectric converter adapted to receive a first light signal and generate an electrical signal according to the first light signal, wherein the first light signal is generated by an object under test by reflecting a second light signal; and
   a voltage control oscillator coupled to the photoelectric converter and adapted to generate an oscillating signal under an injection of the electrical signal, wherein a feedback injection locking function is employed by the voltage control oscillator, a frequency of the oscillating signal is varied and pulled by a variation of the frequency of the electrical signal, the oscillating signal is processed for obtaining movement parameters of the object under test.

20. A wireless detection method comprising:
   receiving a first wireless signal and generating an electrical signal according to the first wireless signal using an antenna, wherein the first wireless signal is generated by reflecting a second wireless signal from an object under test; and
   generating an oscillating signal using a voltage control oscillator under an injection of the electrical signal, wherein a feedback injection locking function is employed by the voltage control oscillator, a frequency of the oscillating signal is varied and pulled by a variation of the frequency of the electrical signal, the oscillating signal transmitted to and being processed by a processing unit to evaluate movement parameters of the object under test.

21. A wireless detection method comprising:
   converting a received first light signal into an electrical signal using a photoelectric converter, wherein the first light signal is generated by reflecting a second light signal from an object under test; and
   generating an oscillating signal using a voltage control oscillator under an injection of the electrical signal, wherein a feedback injection locking function is employed by the voltage control oscillator, a frequency of the oscillating signal is varied and pulled by a variation of the frequency of the electrical signal, the oscillating signal transmitted to and being processed by a processing unit to evaluate movement parameters of the object under test.

* * * * *